United States Patent
Moyerman et al.

(10) Patent No.: US 11,246,530 B2
(45) Date of Patent: Feb. 15, 2022

(54) RESPIRATORY BIOLOGICAL SENSING

(71) Applicant: Intel Corporation, Santa Clara, CA (US)

(72) Inventors: Stephanie Moyerman, Phoenix, AZ (US); James Brian Hall, Tucson, AZ (US); Karolina Karli Cengija, Hillsboro, OR (US); Michael R Rosen, Santa Clara, CA (US); Melissa Ortiz, Campbell, CA (US); Naghma Anwar, San Jose, CA (US); Donald L Gross, Hillsboro, OR (US)

(73) Assignee: Intel Corporation, Santa Clara, CA (US)

( * ) Notice: Subject to any disclaimer, the term of this patent is extended or adjusted under 35 U.S.C. 154(b) by 244 days.

(21) Appl. No.: 15/589,242

(22) Filed: May 8, 2017

(65) Prior Publication Data

US 2018/0317846 A1 Nov. 8, 2018

(51) Int. Cl.
*A61B 5/00* (2006.01)
*A61B 5/08* (2006.01)

(52) U.S. Cl.
CPC .......... *A61B 5/6803* (2013.01); *A61B 5/0022* (2013.01); *A61B 5/0816* (2013.01);
(Continued)

(58) Field of Classification Search
CPC ... A61B 5/6803; A61B 5/6819; A61B 5/6802; A61B 5/6801; A61B 5/0022;
(Continued)

(56) References Cited

U.S. PATENT DOCUMENTS 5,853,005 A * 12/1998 Scanlon ................. A61B 5/113
600/459
2008/0319333 A1* 12/2008 Gavish ..................... A61B 5/08
600/529

(Continued)

FOREIGN PATENT DOCUMENTS

EP 2282797 2/2011

OTHER PUBLICATIONS

Oletic, Dinko, et al., "Low-Power Wearable Respiratory Sound Sensing", Faculty of Electrical Engineering and Computing, University of Zagreb, Unska, (Apr. 9, 2014), 23 pgs.

*Primary Examiner* — Matthew Kremer
*Assistant Examiner* — Avery M Foley
(74) *Attorney, Agent, or Firm* — Schwegman Lundberg & Woessner, P.A.

(57) ABSTRACT

A respiratory sensor system provides the ability to determine a respiration rate. The respiratory sensor system may include a respiratory sensor and a software solution, where the software solution determines respiration rate from the respiratory sensor (e.g., microphone) located on the bridge of the user's nose. The respiratory sensor may be placed on or near the nose, such as a microphone located in the nosepiece of a pair of glasses. Due to the placement of the microphone and the respiration detection system design, the wearer respiration rate can be determined reliably even with ambient noise and movement. This makes the respiration rate calculation accessible and reliable, both for everyday wear and for extreme situations such as sports.

16 Claims, 8 Drawing Sheets

(52) U.S. Cl.
CPC .......... *A61B 5/7257* (2013.01); *A61B 5/7278* (2013.01); *A61B 2562/0204* (2013.01)

(58) Field of Classification Search
CPC ....... A61B 5/0816; A61B 5/0803; A61B 5/08; A61B 5/7257; A61B 5/7278; A61B 2562/0204; G16H 40/67
See application file for complete search history.

(56) References Cited

U.S. PATENT DOCUMENTS

| | | | |
|---|---|---|---|
| 2011/0066064 A1* | 3/2011 | Jangle | A61B 5/0816 |
| | | | 600/534 |
| 2012/0203128 A1 | 8/2012 | Levison et al. | |
| 2014/0091945 A1* | 4/2014 | Rivas | A61B 5/113 |
| | | | 340/870.01 |
| 2014/0228692 A1* | 8/2014 | Chan | A61B 5/08 |
| | | | 600/484 |
| 2014/0276167 A1 | 9/2014 | Dasgupta et al. | |
| 2015/0148628 A1* | 5/2015 | Abreu | A61B 5/0008 |
| | | | 600/316 |
| 2016/0220756 A1* | 8/2016 | Doyle | A61M 5/1723 |
| 2017/0086730 A1* | 3/2017 | Lu | A61B 5/7405 |
| 2018/0104439 A1* | 4/2018 | Tzvieli | A61B 5/0816 |

\* cited by examiner

RESPIRATORY BIOLOGICAL SENSING

TECHNICAL FIELD

Embodiments described herein generally relate to stress sensors.

BACKGROUND

Respiration rate is one of the key vital signs that indicate overall health and wellness. In various examples, respiratory sensors include spirometry airflow sensors, doctor analysis via chest cavity volume or stethoscope, or stretch sensors embedded in clothing. However, these existing solutions for determining respiration rate are bulky, expensive, inaccurate, inaccessible, or time-consuming. It is desirable to provide an improved respiratory sensor for a consumer that is reliable, accessible, convenient, inexpensive, and readily available.

DESCRIPTION OF EMBODIMENTS

A technical solution to the technical problem of determining a respiration rate includes a respiratory sensor and a software solution, where the software solution determines respiration rate from the respiratory sensor (e.g., microphone) located on the bridge of the user's nose. The respiratory sensor may be placed on or near the nose, such as a microphone located in the nosepiece of a pair of glasses. Due to the placement of the microphone and the respiration detection system design, the wearer respiration rate can be determined reliably even with ambient noise (e.g., music) and movement. This makes the respiration rate calculation accessible and reliable, both for everyday wear and for extreme situations such as sports. The respiration detection described herein provides reliable respiration rates within various environments and with various users, and consistently provide respiration rate whenever the nosepiece is in contact with the wearer's face.

The following description and the drawings sufficiently illustrate specific embodiments to enable those skilled in the art to understand the specific embodiment. Other embodiments may incorporate structural, logical, electrical, process, and other changes. Portions and features of various embodiments may be included in, or substituted for, those of other embodiments. Embodiments set forth in the claims encompass all available equivalents of those claims.

Figure 1:
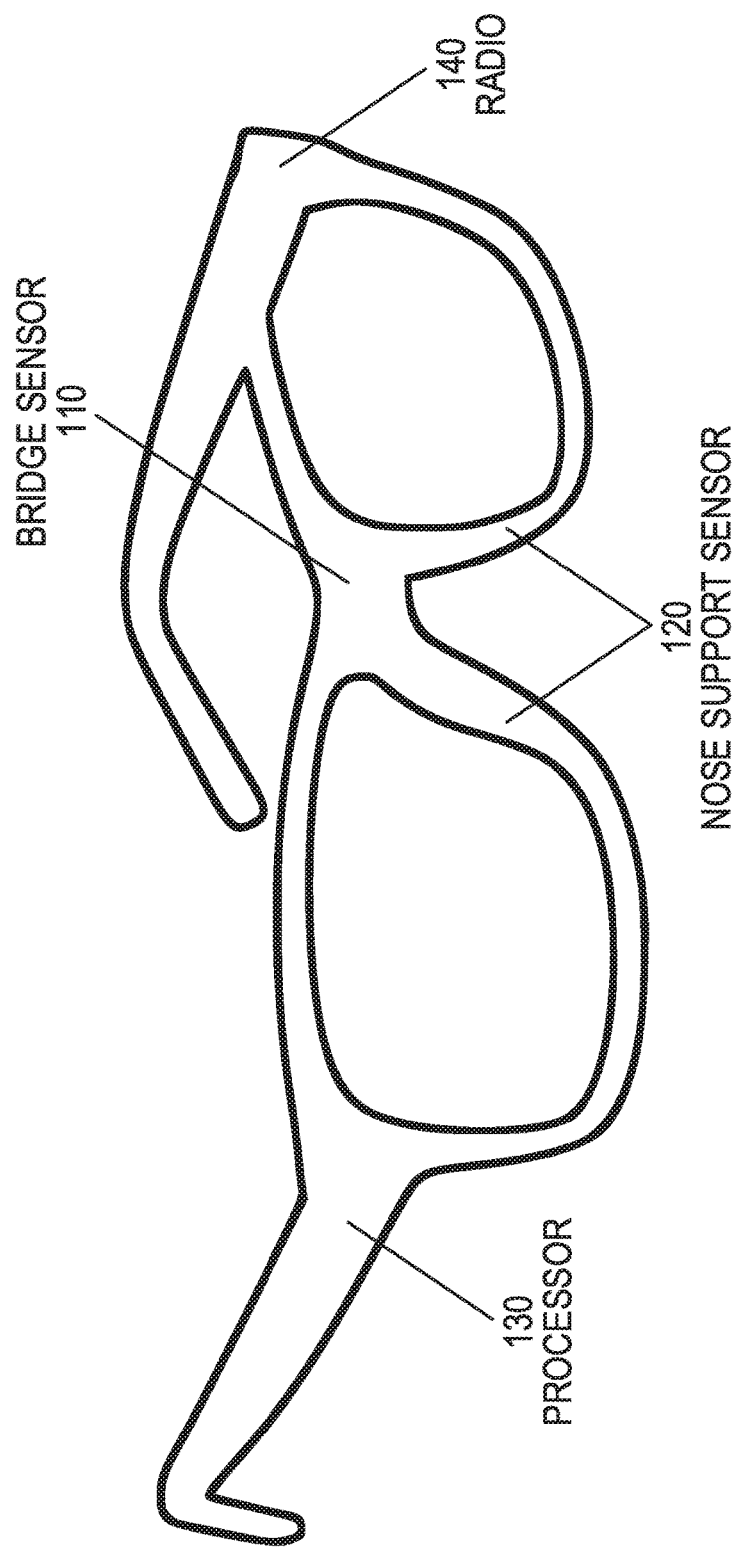
FIG. 1 is a perspective diagram of respiratory sensor eyeglasses, in accordance with at least one embodiment.

FIG. 1 is a perspective diagram of respiratory sensor eyeglasses 100, in accordance with at least one embodiment. Respiratory sensor eyeglasses 100 may detect respiration rate using a sensor within the glasses bridge 110 or within the nose support 120. FIG. 1 shows the nose support sensor 120 within the eyeglasses frames, however the nose support sensor 120 may be partially or completely within nose pads, nose pad supports, or related eyeglasses support structures. Nose support sensor 120 may include two sensors on each side of the nose, or may include a single sensor on a left or right side of the nose. The bridge sensor 110 or the nose support sensor 120 may include a transducer that converts vibration (e.g., breathing) into electrical signals. The transducers may include one or more of a vibration transducer or an acoustic transducer, such as a piezoelectric microphone, a microelectromechanical systems (MEMS) microphone, or other types of transducers.

In an embodiment, the respiration detection system includes a respiration detection process that is implemented on a processor 130 embedded within the glasses. As described below, the respiration detection process may use batch processing and a computationally efficient fast Fourier transform (FFT) to provide reliable respiratory calculations while remaining computationally lightweight. The resulting respiration detection process is light in memory and processor requirements, enabling the respiration detection process to run on an embedded processor 130, thereby avoiding the need for transmission of the raw audio signal to a phone, tablet, or other connected mobile electronic device. Alternatively or in addition to processing data on processor 130, respiration data may be provided through a radio 140 (e.g., Bluetooth connection) to a connected mobile electronic device.

Processor 130, radio 140, a power source, and other electronics may be located in various places within the eyeglasses frames, such as to improve eyeglasses balance or comfort. The presence of a transducer and related electronics within eyeglasses may be an indication of potentially infringing devices. The implementation of various components of the respiratory sensor eyeglasses 100 allows the technology to be integrated into everyday eyewear, while still providing reliable respiration rate determination in a hidden and unobtrusive way.

Figure 2:
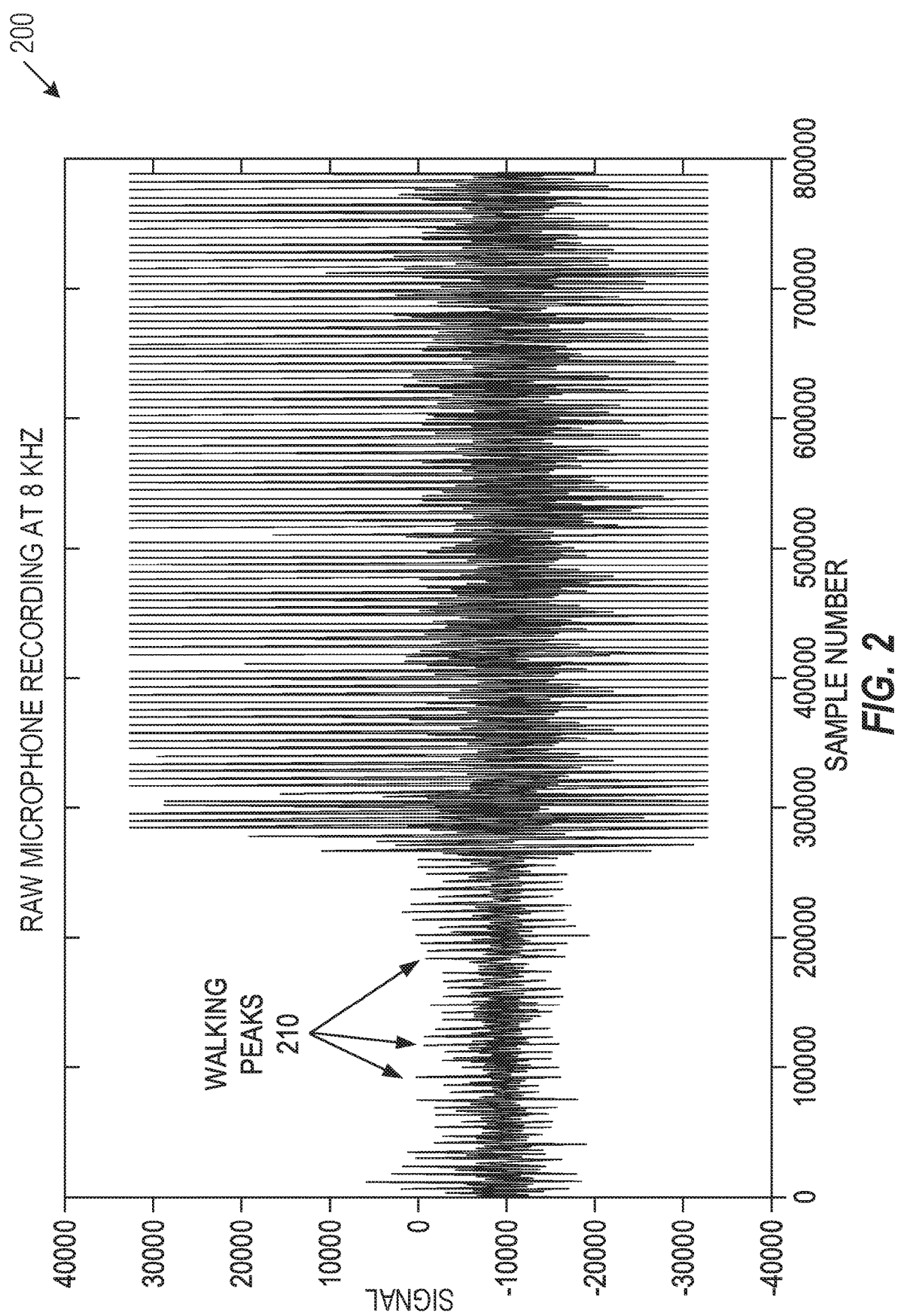
FIG. 2 is a graph of respiratory audio sample, in accordance with at least one embodiment.

FIG. 2 is a graph of respiratory audio sample 200, in accordance with at least one embodiment. The audio sample 200 shows the raw output of a piezoelectric microphone located in a nose bridge of a pair of eyeglasses. The microphone output was recorded at a sample rate of 8 KHz. The audio sample 200 was recorded while a user was walking. The audio sample 200 is noisy, contaminated by the user walking (i.e., sharp walking peaks 210 throughout) and other ambient noise (i.e., the baseline fluctuations). Detection of the respiration rate is improved by analyzing the audio sample 200 in the frequency domain, such as shown in FIG. 3.

Figure 3:
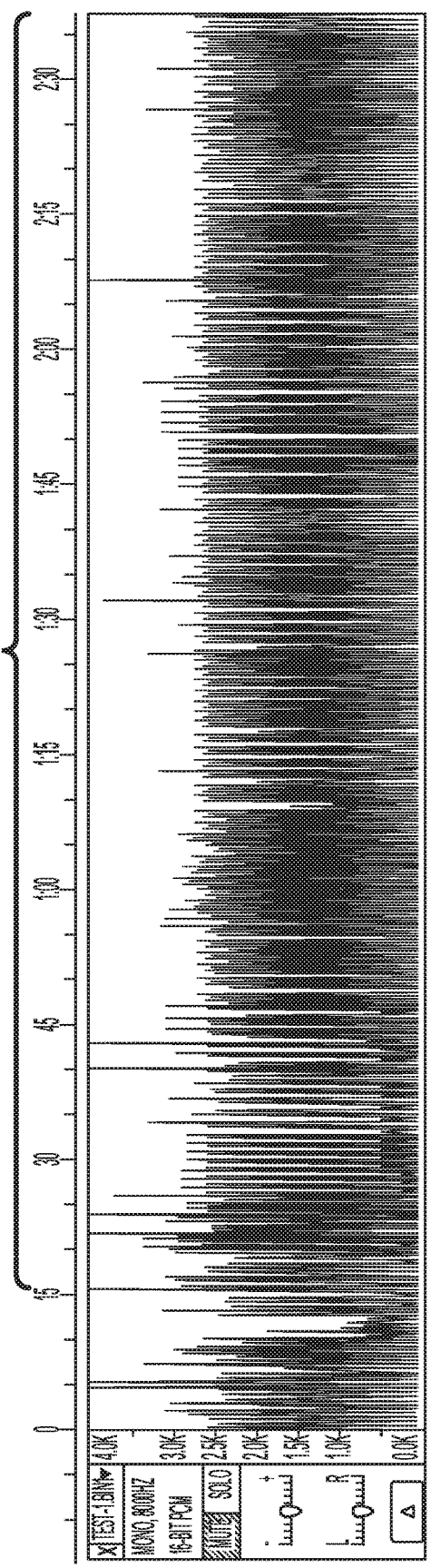
FIG. 3 is a graph of respiratory audio frequency data, in accordance with at least one embodiment.
Figure 3:
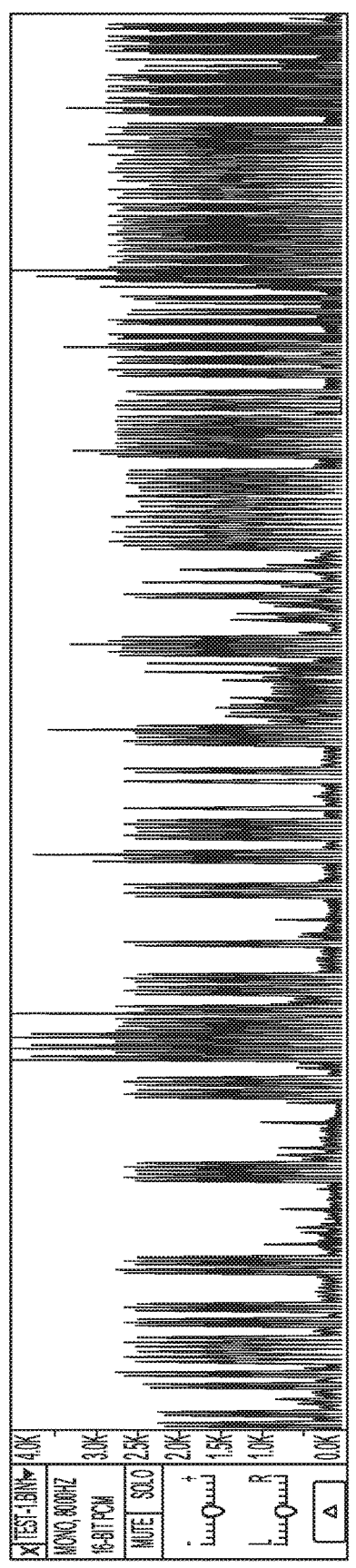

FIG. 3 is a graph of respiratory audio frequency data 300, in accordance with at least one embodiment. The respiratory audio frequencies 300 include the raw output of the piezoelectric microphone shown in FIG. 2, where the raw output has been shifted to the frequency domain. In particular, frequency data 300 includes a walking and breathing portion 310 that uses the same raw data as shown in FIG. 2. Frequency data 300 also shows a breathing-only portion 320 that includes occasional breath-holding pauses. Frequency data 300 also shows a combination breathing and music portion 330. Each plot within frequency data 300 shows the breath signal (i.e., inhalation or exhalation) that is readily observed in the 800-2500 Hz band, despite the contamination seen in the time domain shown in FIG. 2. In some embodiments, the strongest frequency peaks within the frequency data 300 are in or around a breathing frequency range of 2000-2300 Hz. For example, human motion may provide a contaminant (e.g., false positive) audio signal output during a time when there is no obvious breathing, but the respiration detection process may exclude the human motion signals and detect respiration rate by focusing the respiration detection process on breathing frequency range of approximately 2000-2300 Hz. Each plot within frequency data 300 was generated using a 256-point rolling fast Fourier transform (FFT) with a Hanning window smoother applied to each sample, though other frequency transformations or window functions may be used. The frequency data 300 may be used to detect a respiratory rate, such as using the respiratory processing flow chart shown in FIG. 4.

Figure 4:
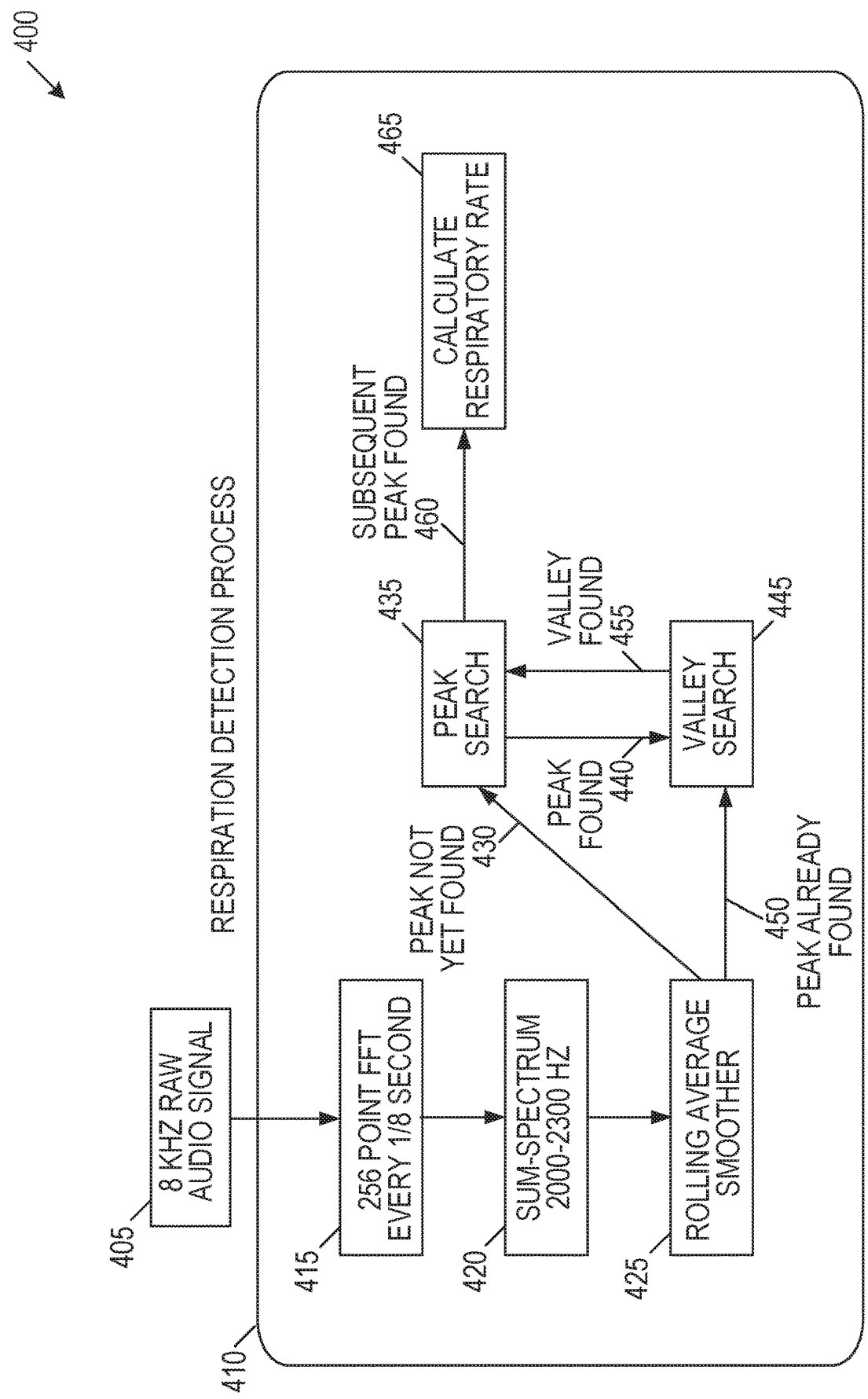
FIG. 4 is a respiratory processing flow chart, in accordance with at least one embodiment.

FIG. 4 is a respiratory processing flow chart 400, in accordance with at least one embodiment. Respiratory processing flow chart 400 receives an 8 kHz raw signal input 405 as input to the respiration detection process 410, such as from a microphone mounted in the bridge of eyeglasses. Input 405 is frequency-transformed 415 using a 256-point ITT with a Hanning window smoother. Frequency transformation 415 may be performed as samples become available or may be batch-processed, such as batch processing samples every $\frac{1}{8}^{th}$ of a second (e.g., approximately 2000 samples). The output of the frequency transformation 415 is provided to a spectrum summation 420, where the spectrum summation 420 sums breathing signals within a predetermined frequency range, such as within a breathing frequency range of 2000-2300 Hz. To reduce or eliminate spurious peaks or outlier data points, the summed output of the spectrum summation 420 is smoothed 425, such as using a 3-point rolling average of the summed output.

After smoothing 425, respiratory processing flow chart 400 branches based on the current state of a system. When receiving the first set of data from the smoother 425, the peak is not yet found 430, and the flow chart 400 branches to a peak search 435. The peak search 435 may also be conducted between detected inhalation or exhalation peaks, such as when the user is holding his or her breath. During the peak search 435, the system looks for a data peak to determine respiratory rate, where the data peak may be defined using various criteria. In various embodiments, the criteria used to identify a data peak includes one or more of a data point whose magnitude is higher than the three preceding and three following data points, a data point that exceeds a predetermined threshold (e.g., an empirically derived threshold), or a data point that is within 20% of the value of the last peak. When receiving the first set of data from the smoother operation 425, the initialized value of the last peak is set to 10,000. These data peak identification criteria may be selected to reduce or eliminate spurious noise within the breathing frequency band from manifesting as false peaks within the data from the smoother operation 425.

Once the peak search 435 indicates that a peak has been found 440, it branches to the valley search 445, where a data valley may be defined using various criteria. In various embodiments, the criteria used to identify a data valley includes one or more of a data point that is lower than the two preceding and two following points in time, or a data point that is less than 40% of the preceding peak value. These data valley identification criteria may be selected to reduce or eliminate spurious valleys from manifesting as false valleys within the data. A valley search 445 may also be performed on additional data received from the smoother operation 425 when at least a first peak has already been identified 450.

In an embodiment, the respiration rate is calculated based on at least two peaks. Once the valley search 445 identifies a data valley has been found 455, the respiration detection process branches to search for a subsequent peak using the peach search 435. Once a subsequent peak is identified 460, the respiration rate is calculated 465 based on the time difference between any two peaks. In particular, because subsequent peak times coincide with successive inhalations and exhalations, the respiration rate is calculated 465 as twice the time between any two consecutive peaks. For example, this calculation 465 corresponds to the time between the midpoint of an inhalation and the midpoint of an exhalation (or vice-versa), including any breathing pause between inhalation and exhalation. In various embodiments, the respiration rate may be calculated based on a moving average of multiple peak-to-peak time measurements. An example of calculated respiratory rate 465 is shown in FIG. 5.

Figure 5:
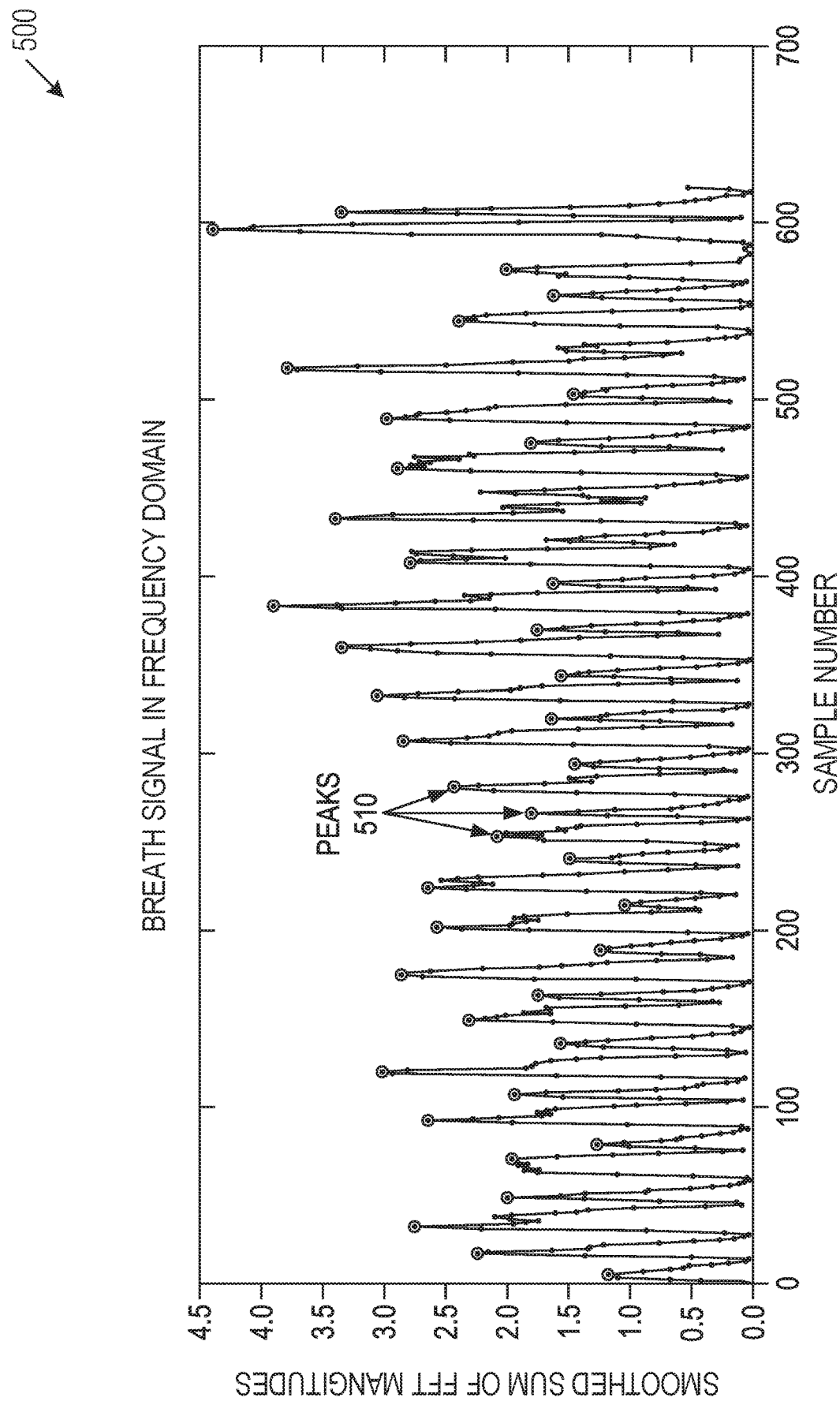
FIG. 5 is a graph of smoothed respiratory data, in accordance with at least one embodiment.

FIG. 5 is a graph of smoothed respiratory data 500, in accordance with at least one embodiment. Smoothed respiratory data 500 shows the smoothed moving average of the sum of the FFT magnitudes within the 2000-2300 HZ frequency range. As described above, by finding peaks and the valleys within the data, the periods of inhalation and exhalation can be identified. Multiple successive peaks 510 are depicted using circles, and the respiration rate is calculated as double the time between successive peaks 510. Additional data points shown within the smoothed respiratory data 500 correspond to smoothed data, each separated by ⅛ second. Based on the peaks shown within the smoothed respiratory data 500, the user is breathing in a rhythmic pattern of inhalation and exhalation at a cadence of approximately 1.25 seconds. While the smoothed respiratory data 500 includes multiple peaks in close proximity, the effect of irregular breathing is shown in FIG. 6.

Figure 6:
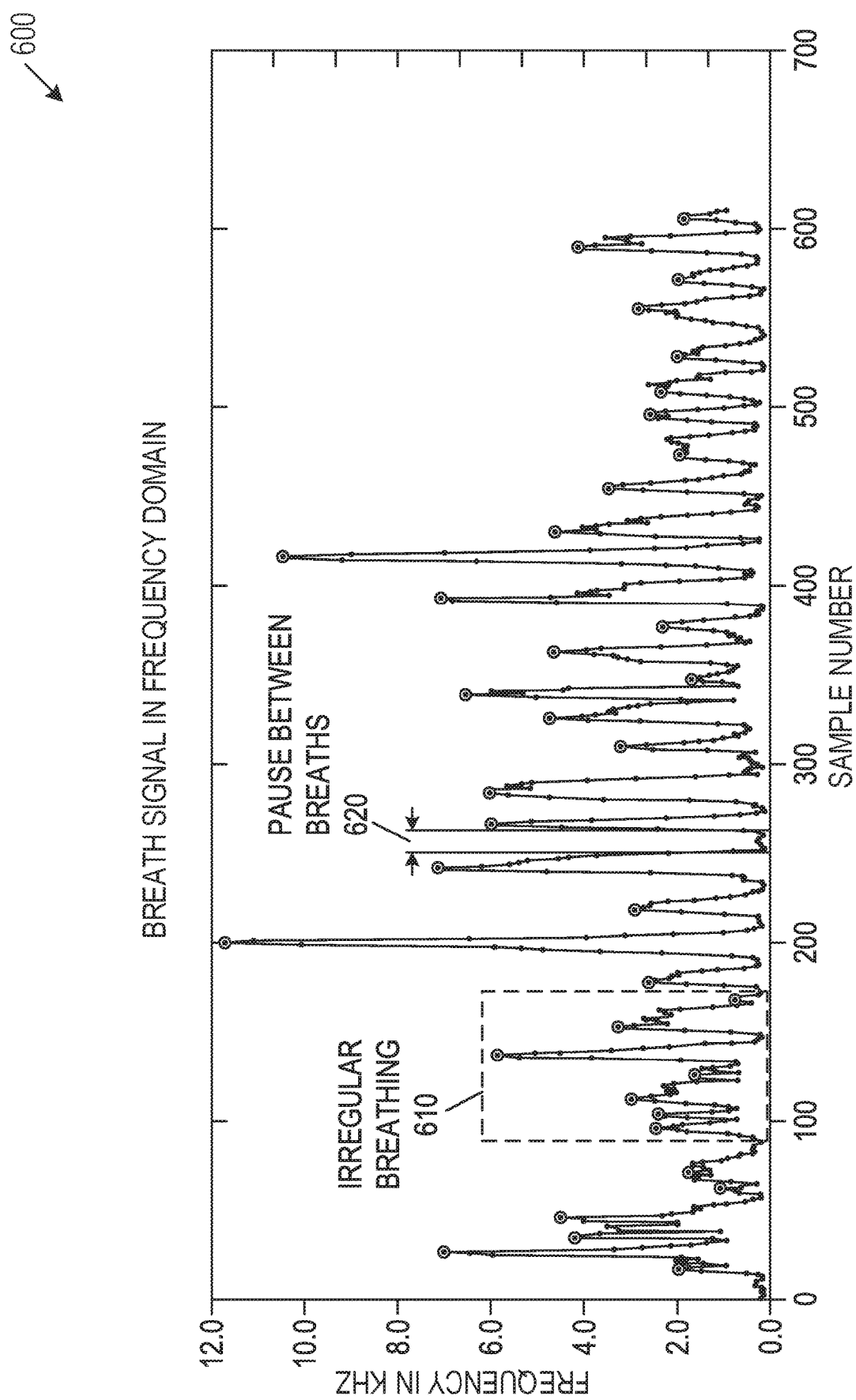
FIG. 6 is a graph of irregular respiratory data, in accordance with at least one embodiment.

FIG. 6 is a graph of irregular respiratory data 600, in accordance with at least one embodiment. Irregular respiratory data 600 shows regions of irregular breathing 605, which may include fast-interspersed breaths. Irregular respiratory data 600 also shows regions of pauses between breaths 620. The relative magnitudes of peaks and time delays between successive peaks may vary among users, where the variations may be affected by user breathing patterns, sensor placement (i.e., eyeglasses placement), and other user-specific variations. The respiration detection process may begin by using a relatively low threshold for audio signal peaks, such as by including frequencies below or above the expected breathing spectrum of 2.0-2.3 kHz. As additional peaks are detected, the audio signal breathing spectrum may be narrowed to 2.0-2.3 kHz or narrower. The respiration detection process may recalibrate the audio signal breathing spectrum or other respiration rate calculation thresholds in response to excessive peak noise or excessively pauses between breaths (e.g., temporarily removing glasses). Various recalibration or outlier rejection thresholds may be used for excessive peak noise or excessively long pauses between breaths. For example, a lower peak noise threshold may be used to detect a peak event that causes the audio signal breathing spectrum to be narrowed to 2.0-2.3 kHz, and a higher peak noise threshold may be used to identify and exclude outlier peaks. By reducing or eliminating spurious peaks, valleys, or other outlier data points, the respiration detection process is still able to identify peaks and determine the respiration rate.

Figure 7:
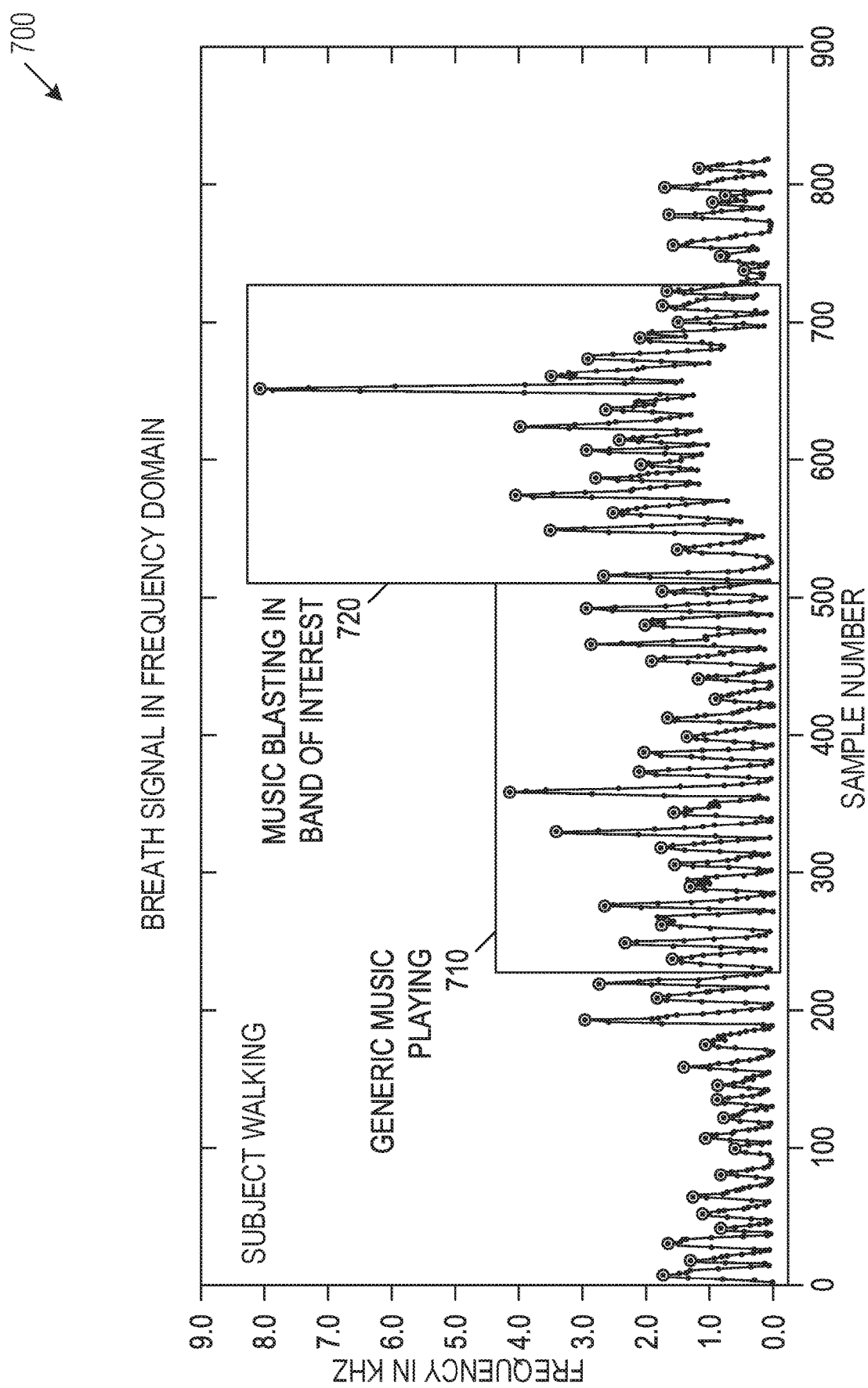
FIG. 7 is a graph of increased noise respiratory data, in accordance with at least one embodiment.

FIG. 7 is a graph of increased noise respiratory data 700, in accordance with at least one embodiment. Increased noise respiratory data 700 was collected while the user was simultaneously walking and listening to music. Two regions included targeted testing, where audio pitches in the 1.5-2 kHz region were directed toward the user. The first region 710 represents a period that included generic music playing. While generic music was playing, the detected frequencies of the various peaks were increased, however the respiration detection process was still able to identify peaks and determine the respiration rate. The second region 720 represents a period that included music blasting in the frequencies of interest. While generic music was blasting, the detected frequencies of the various peaks and valleys (i.e., noise floor) were increased, however the respiration detection process was still able to identify peaks and determine the respiration rate.

Figure 8:
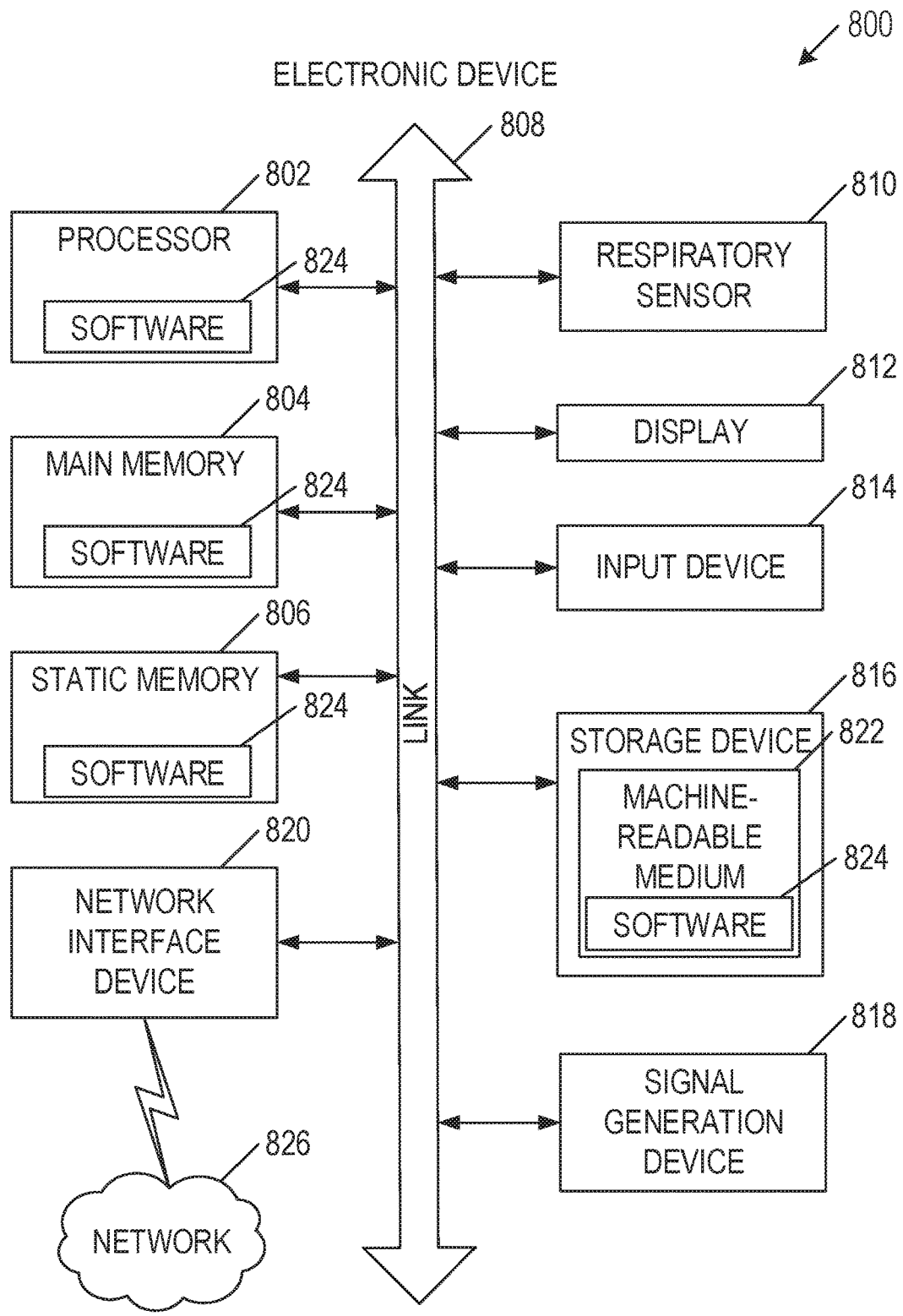
FIG. 8 is a block diagram illustrating a respiratory sensor in the example form of an electronic device, according to an example embodiment.

FIG. 8 is a block diagram illustrating a respiratory sensor system in the example form of an electronic device 800, within which a set or sequence of instructions may be executed to cause the machine to perform any one of the methodologies discussed herein, according to an example embodiment. Electronic device 800 may also represent the device shown in FIG. 1. In alternative embodiments, the electronic device 800 operates as a standalone device or may be connected (e.g., networked) to other machines. In a networked deployment, the electronic device 800 may operate in the capacity of either a server or a client machine in server-client network environments, or it may act as a peer machine in peer-to-peer (or distributed) network environments. The electronic device 800 may be electronic glasses, an integrated circuit (IC), a portable electronic device, a personal computer (PC), a tablet PC, a hybrid tablet, a personal digital assistant (PDA), a mobile telephone, or any electronic device 800 capable of executing instructions (sequential or otherwise) that specify actions to be taken by that machine to detect a user input. Further, while only a single electronic device 800 is illustrated, the terms "machine" or "electronic device" shall also be taken to include any collection of machines or devices that individually or jointly execute a set (or multiple sets) of instructions to perform any one or more of the methodologies discussed herein. Similarly, the term "processor-based system" shall be taken to include any set of one or more machines that are controlled by or operated by a processor (e.g., a computer) to execute instructions, individually or jointly, to perform any one or more of the methodologies discussed herein.

Example electronic device 800 includes at least one processor 802 (e.g., a central processing unit (CPU), a graphics processing unit (GPU) or both, processor cores, compute nodes, etc.), a main memory 804 and a static memory 806, which communicate with each other via a link 808 (e.g., bus).

The electronic device 800 includes a respiratory sensor 810, where the respiratory sensor 810 may include audio or vibration transducers as described above. The electronic device 800 may further include a display unit 812, where the display unit 812 may include a single component that provides a user-readable display and a protective layer, or another display type. The electronic device 800 may further include an input device 814, such as a pushbutton, a keyboard, an NFC card reader, or a user interface (UI) navigation device (e.g., a touch-sensitive input). The electronic device 800 may additionally include a storage device 816, such as a solid-state drive (SSD) unit. The electronic device 800 may additionally include a signal generation device 818 to provide audible or visual feedback, such as a speaker to provide an audible feedback or one or more LEDs to provide a visual feedback. The electronic device 800 may additionally include a network interface device 820, and one or more additional sensors (not shown), such as a global positioning system (GPS) sensor, compass, accelerometer, or other sensor.

The storage device 816 includes a machine-readable medium 822 on which is stored one or more sets of data structures and instructions 824 (e.g., software) embodying or utilized by any one or more of the methodologies or functions described herein. The instructions 824 may also reside, completely or at least partially, within the main memory 804, static memory 806, and/or within the processor 802 during execution thereof by the electronic device 800. The main memory 804, static memory 806, and the processor 802 may also constitute machine-readable media.

While the machine-readable medium 822 is illustrated in an example embodiment to be a single medium, the term "machine-readable medium" may include a single medium or multiple media (e.g., a centralized or distributed database, and/or associated caches and servers) that store the one or more instructions 824. The term "machine-readable medium" shall also be taken to include any tangible medium that is capable of storing, encoding or carrying instructions for execution by the machine and that cause the machine to perform any one or more of the methodologies of the present disclosure or that is capable of storing, encoding or carrying data structures utilized by or associated with such instructions. The term "machine-readable medium" shall accordingly be taken to include, but not be limited to, solid-state memories, and optical and magnetic media. Specific examples of machine-readable media include non-volatile memory, including but not limited to, by way of example, semiconductor memory devices (e.g., electrically programmable read-only memory (EPROM), electrically erasable programmable read-only memory (EEPROM)) and flash memory devices; magnetic disks such as internal hard disks and removable disks; magneto-optical disks; and CD-ROM and DVD-ROM disks.

The instructions 824 may further be transmitted or received over a communications network 826 using a transmission medium via the network interface device 820 utilizing any one of a number of well-known transfer protocols (e.g., HTTP). Examples of communication networks include a local area network (LAN), a wide area network (WAN), the Internet, mobile telephone networks, and wireless data networks (e.g., Wi-Fi, NFC, Bluetooth, Bluetooth LE, 3G, 5G LTE/LTE-A, WiMAX networks, etc.). The term "transmission medium" shall be taken to include any intangible medium that is capable of storing, encoding, or carrying instructions for execution by the machine, and includes digital or analog communications signals or other intangible medium to facilitate communication of such software.

To better illustrate the method and apparatuses disclosed herein, a non-limiting list of embodiments is provided here.

Example 1 is a respiratory rate detection system comprising: a transducer disposed within a pair of eyeglasses to detect respiration and generate a respiration signal; and a processor to receive the respiration signal from the transducer and determine a respiration rate.

In Example 2, the subject matter of Example 1 optionally includes wherein the transducer is disposed within a bridge region within the pair of eyeglasses.

In Example 3, the subject matter of any one or more of Examples 1-2 optionally include wherein the transducer is disposed within a nose support region within the pair of eyeglasses.

In Example 4, the subject matter of any one or more of Examples 1-3 optionally include wherein the processor is disposed within the pair of eyeglasses.

In Example 5, the subject matter of any one or more of Examples 1-4 optionally include a wireless radio disposed within the pair of eyeglasses, the wireless radio to transmit the respiration signal from the transducer to an electronic device separate from the pair of eyeglasses, wherein the processor is disposed within the electronic device.

In Example 6, the subject matter of any one or more of Examples 1-5 optionally include wherein the transducer includes an audible signal transducer.

In Example 7, the subject matter of any one or more of Examples 1-6 optionally include wherein the transducer includes a vibration signal transducer.

In Example 8, the subject matter of any one or more of Examples 1-7 optionally include the processor further to process the received respiration signal and identify a plurality of inhalation/exhalation peaks, wherein identifying the plurality of inhalation/exhalation peaks includes identifying at least a first respiration peak and a second respiration peak.

In Example 9, the subject matter of Example 8 optionally includes wherein the respiration rate is determined based on a peak time delay between the first respiration peak and the second respiration peak.

In Example 10, the subject matter of Example 9 optionally includes wherein the respiration rate is calculated as double the peak time delay between the first respiration peak and the second respiration peak.

In Example 11, the subject matter of any one or more of Examples 8-10 optionally include wherein identifying the plurality of inhalation/exhalation peaks includes applying a data peak criteria to the received respiration signal.

In Example 12, the subject matter of Example 11 optionally includes wherein the data peak criteria includes at least one of identifying a local maximum data point whose magnitude is higher than a group of three preceding and higher than a group of three following data points, identifying a threshold data point whose magnitude exceeds a predetermined threshold, and identifying a consistent data point whose magnitude is within twenty percent of a previous data point.

In Example 13, the subject matter of any one or more of Examples 8-12 optionally include wherein identifying the second respiration peak includes identifying a first valley between the first respiration peak and the second respiration peak.

In Example 14, the subject matter of any one or more of Examples 8-13 optionally include wherein identifying the first valley includes applying a data valley criteria to the received respiration signal.

In Example 15, the subject matter of Example 14 optionally includes wherein the data valley criteria includes at least one of identifying a local minimum data point whose magnitude is lower than a group of two preceding and lower than a group of two following data points, and identifying a discontinuous data point whose magnitude is less than forty percent of a previous peak data point.

In Example 16, the subject matter of any one or more of Examples 1-15 optionally include the processor further to frequency-transform the respiration signal to generate a frequency-transformed signal.

In Example 17, the subject matter of Example 16 optionally includes the processor further to apply a window smoother to the frequency-transformed signal to generate a windowed frequency signal.

In Example 18, the subject matter of Example 17 optionally includes the processor further to apply a spectrum summation to the windowed frequency signal to generate a summed spectrum signal.

In Example 19, the subject matter of Example 18 optionally includes wherein the spectrum summation includes a frequency window range of 2000 HZ to 2300 Hz.

In Example 20, the subject matter of any one or more of Examples 18-19 optionally include the processor further to apply a smoothing average to the summed spectrum signal to generate a smoothed summed signal.

Example 21 is a respiratory rate detection method comprising: generating a respiration signal from a transducer disposed within a pair of eyeglasses; and determining a respiration rate based on the respiration signal.

In Example 22, the subject matter of Example 21 optionally includes wherein the transducer is disposed within a bridge region within the pair of eyeglasses.

In Example 23, the subject matter of any one or more of Examples 21-22 optionally include wherein the transducer is disposed within a nose support region within the pair of eyeglasses.

In Example 24, the subject matter of any one or more of Examples 21-23 optionally include wherein the processor is disposed within the pair of eyeglasses.

In Example 25, the subject matter of any one or more of Examples 21-24 optionally include transmitting the respiration signal from the transducer via a wireless radio disposed within the pair of eyeglasses to an electronic device separate from the pair of eyeglasses, wherein the processor is disposed within the electronic device.

In Example 26, the subject matter of any one or more of Examples 21-25 optionally include wherein the transducer includes an audible signal transducer.

In Example 27, the subject matter of any one or more of Examples 21-26 optionally include wherein the transducer includes a vibration signal transducer.

In Example 28, the subject matter of any one or more of Examples 21-27 optionally include identifying a plurality of inhalation/exhalation peaks, wherein identifying the plurality of inhalation/exhalation peaks includes identifying at least a first respiration peak and a second respiration peak.

In Example 29, the subject matter of Example 28 optionally includes wherein determining the respiration rate is based on a peak time delay between the first respiration peak and the second respiration peak.

In Example 30, the subject matter of Example 29 optionally includes wherein determining the respiration rate includes calculating the respiration rate as double the peak time delay between the first respiration peak and the second respiration peak.

In Example 31, the subject matter of any one or more of Examples 28-30 optionally include wherein identifying the plurality of inhalation/exhalation peaks includes applying a data peak criteria to the received respiration signal.

In Example 32, the subject matter of Example 31 optionally includes wherein the data peak criteria includes at least one of identifying a local maximum data point whose magnitude is higher than a group of three preceding and higher than a group of three following data points, identifying a threshold data point whose magnitude exceeds a predetermined threshold, and identifying a consistent data point whose magnitude is within twenty percent of a previous data point.

In Example 33, the subject matter of any one or more of Examples 28-32 optionally include wherein identifying the second respiration peak includes identifying a first valley between the first respiration peak and the second respiration peak.

In Example 34, the subject matter of any one or more of Examples 28-33 optionally include wherein identifying the first valley includes applying a data valley criteria to the received respiration signal.

In Example 35, the subject matter of Example 34 optionally includes wherein the data valley criteria includes at least one of identifying a local minimum data point whose magnitude is lower than a group of two preceding and lower than a group of two following data points, and identifying a discontinuous data point whose magnitude is less than forty percent of a previous peak data point.

In Example 36, the subject matter of any one or more of Examples 21-35 optionally include frequency-transforming the respiration signal to generate a frequency-transformed signal.

In Example 37, the subject matter of Example 36 optionally includes applying a window smoother to the frequency-transformed signal to generate a windowed frequency signal.

In Example 38, the subject matter of Example 37 optionally includes applying a spectrum summation to the windowed frequency signal to generate a summed spectrum signal.

In Example 39, the subject matter of Example 38 optionally includes wherein the spectrum summation includes a frequency window range of 2000 Hz to 2300 Hz.

In Example 40, the subject matter of any one or more of Examples 38-39 optionally include applying a smoothing average to the summed spectrum signal to generate a smoothed summed signal.

Example 41 is at least one machine-readable medium including instructions, which when executed by a computing system, cause the computing system to perform any of the methods of Examples 21-40.

Example 42 is an apparatus comprising means for performing any of the methods of Examples 21-40.

Example 43 is at least one machine-readable storage medium, comprising a plurality of instructions that, responsive to being executed with processor circuitry of a computer-controlled device, cause the computer-controlled device to: generate a respiration signal from a transducer disposed within a pair of eyeglasses; and determine a respiration rate based on the respiration signal.

In Example 44, the subject matter of Example 43 optionally includes wherein the transducer is disposed within a bridge region within the pair of eyeglasses.

In Example 45, the subject matter of any one or more of Examples 43-44 optionally include wherein the transducer is disposed within a nose support region within the pair of eyeglasses.

In Example 46, the subject matter of any one or more of Examples 43-45 optionally include wherein the processor is disposed within the pair of eyeglasses.

In Example 47, the subject matter of any one or more of Examples 43-46 optionally include wherein the instructions further cause the computer-controlled device to transmit the respiration signal from the transducer via a wireless radio disposed within the pair of eyeglasses to an electronic device separate from the pair of eyeglasses, wherein the processor is disposed within the electronic device.

In Example 48, the subject matter of any one or more of Examples 43-47 optionally include wherein the transducer includes an audible signal transducer.

In Example 49, the subject matter of any one or more of Examples 43-48 optionally include wherein the transducer includes a vibration signal transducer.

In Example 50, the subject matter of any one or more of Examples 43-49 optionally include wherein the instructions further cause the computer-controlled device to identify a plurality of inhalation/exhalation peaks, wherein the instructions further causing the computer-controlled device to identify the plurality of inhalation/exhalation peaks includes the instructions further causing the computer-controlled device to identify at least a first respiration peak and a second respiration peak.

In Example 51, the subject matter of Example 50 optionally includes wherein determining the respiration rate is based on a peak time delay between the first respiration peak and the second respiration peak.

In Example 52, the subject matter of Example 51 optionally includes wherein determining the respiration rate includes calculating the respiration rate as double the peak time delay between the first respiration peak and the second respiration peak.

In Example 53, the subject matter of any one or more of Examples 50-52 optionally include wherein identifying the plurality of inhalation/exhalation peaks includes applying a data peak criteria to the received respiration signal.

In Example 54, the subject matter of Example 53 optionally includes wherein the data peak criteria includes at least one of identifying a local maximum data point whose magnitude is higher than a group of three preceding and higher than a group of three following data points, identifying a threshold data point whose magnitude exceeds a predetermined threshold, and identifying a consistent data point whose magnitude is within twenty percent of a previous data point.

In Example 55, the subject matter of any one or more of Examples 50-54 optionally include wherein identifying the second respiration peak includes identifying a first valley between the first respiration peak and the second respiration peak.

In Example 56, the subject matter of any one or more of Examples 50-55 optionally include wherein identifying the first valley includes applying a data valley criteria to the received respiration signal.

In Example 57, the subject matter of Example 56 optionally includes wherein the data valley criteria includes at least one of identifying a local minimum data point whose magnitude is lower than a group of two preceding and lower than a group of two following data points, and identifying a discontinuous data point whose magnitude is less than forty percent of a previous peak data point.

In Example 58, the subject matter of any one or more of Examples 43-57 optionally include wherein the instructions further cause the computer-controlled device to frequency-transform the respiration signal to generate a frequency-transformed signal.

In Example 59, the subject matter of Example 58 optionally includes wherein the instructions further cause the computer-controlled device to apply a window smoother to the frequency-transformed signal to generate a windowed frequency signal.

In Example 60, the subject matter of Example 59 optionally includes wherein the instructions further cause the computer-controlled device to apply a spectrum summation to the windowed frequency signal to generate a summed spectrum signal.

In Example 61, the subject matter of Example 60 optionally includes wherein the spectrum summation includes a frequency window range of 2000 Hz to 2300 Hz.

In Example 62, the subject matter of any one or more of Examples 60-61 optionally include wherein the instructions further cause the computer-controlled device to apply a smoothing average to the summed spectrum signal to generate a smoothed summed signal.

Example 63 is a respiratory rate detection apparatus comprising: means for generating a respiration signal from a transducer disposed within a pair of eyeglasses; and means for determining a respiration rate based on the respiration signal.

In Example 64, the subject matter of Example 63 optionally includes wherein the transducer is disposed within a bridge region within the pair of eyeglasses.

In Example 65, the subject matter of any one or more of Examples 63-64 optionally include wherein the transducer is disposed within a nose support region within the pair of eyeglasses.

In Example 66, the subject matter of any one or more of Examples 63-65 optionally include wherein the processor is disposed within the pair of eyeglasses.

In Example 67, the subject matter of any one or more of Examples 63-66 optionally include means for transmitting the respiration signal from the transducer via a wireless radio disposed within the pair of eyeglasses to an electronic device separate from the pair of eyeglasses, wherein the processor is disposed within the electronic device.

In Example 68, the subject matter of any one or more of Examples 63-67 optionally include wherein the transducer includes an audible signal transducer.

In Example 69, the subject matter of any one or more of Examples 63-68 optionally include wherein the transducer includes a vibration signal transducer.

In Example 70, the subject matter of any one or more of Examples 63-69 optionally include means for identifying a plurality of inhalation/exhalation peaks, wherein means for identifying the plurality of inhalation/exhalation peaks includes means for identifying at least a first respiration peak and a second respiration peak.

In Example 71, the subject matter of Example 70 optionally includes wherein means for determining the respiration rate is based on a peak time delay between the first respiration peak and the second respiration peak.

In Example 72, the subject matter of Example 71 optionally includes wherein means for determining the respiration rate includes calculating the respiration rate as double the peak time delay between the first respiration peak and the second respiration peak.

In Example 73, the subject matter of any one or more of Examples 70-72 optionally include wherein means for identifying the plurality of inhalation/exhalation peaks includes means for applying a data peak criteria to the received respiration signal.

In Example 74, the subject matter of Example 73 optionally includes wherein the data peak criteria includes at least one of identifying, a local maximum data point whose magnitude is higher than a group of three preceding and higher than a group of three following data points, identifying a threshold data point whose magnitude exceeds a predetermined threshold, and identifying a consistent data point whose magnitude is within twenty percent of a previous data point.

In Example 75, the subject matter of any one or more of Examples 70-74 optionally include wherein means for identifying the second respiration peak includes means for identifying a first valley between the first respiration peak and the second respiration peak.

In Example 76, the subject matter of any one or more of Examples 70-75 optionally include wherein means for identifying the first valley includes means for applying a data valley criteria to the received respiration signal.

In Example 77, the subject matter of Example 76 optionally includes wherein the data valley criteria includes at least one of identifying a local minimum data point whose magnitude is lower than a group of two preceding and lower than a group of two following data points, and identifying a discontinuous data point whose magnitude is less than forty percent of a previous peak data point.

In Example 78, the subject matter of any one or more of Examples 63-77 optionally include means for frequency-transforming the respiration signal to generate a frequency-transformed signal.

In Example 79, the subject matter of Example 78 optionally includes means for applying a window smoother to the frequency-transformed signal to generate a windowed frequency signal.

In Example 80, the subject matter of Example 79 optionally includes means for applying a spectrum summation to the windowed frequency signal to generate a summed spectrum signal.

In Example 81, the subject matter of Example 80 optionally includes wherein the spectrum summation includes a frequency window range of 2000 Hz to 2300 Hz.

In Example 82, the subject matter of any one or more of Examples 80-81 optionally include means for applying a smoothing average to the summed spectrum signal to generate a smoothed summed signal.

Example 83 is at least one machine-readable medium including instructions, which when executed by a machine, cause the machine to perform operations of any of the operations of Examples 1-82.

Example 84 is an apparatus comprising means for performing any of the operations of Examples 1-82.

Example 85 is a system to perform the operations of any of the Examples 1-82.

Example 86 is a method to perform the operations of any of the Examples 1-82.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to allow the reader to quickly ascertain the nature of the technical disclosure. It is submitted with the understanding that it will not be used to interpret or limit the scope or meaning of the claims. In the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The invention claimed is:

1. A respiratory rate detection system comprising:
   an audio transducer disposed within a pair of eyeglasses to detect respiration and generate a respiration signal; and
   a processor to:
   receive the respiration signal from the audio transducer;
   frequency-transform the respiration signal to generate frequency-transformed signals;
   sum magnitudes of the frequency-transformed signals within a breathing frequency range to generate a summed frequency respiration signal, the breathing frequency range including a minimum frequency of at least 2000 Hz and a maximum frequency of at most 2300 Hz;
   identify a first respiration peak and a second respiration peak within the summed frequency respiration signal; and
   determine a respiration rate calculated as double a peak time delay between the first respiration peak and the second respiration peak.

2. The system of claim 1, wherein the audio transducer is disposed within a bridge region within the pair of eyeglasses.

3. The system of claim 1, wherein the audio transducer is disposed within a nose support region within the pair of eyeglasses.

4. The system of claim 1, wherein the processor is disposed within the pair of eyeglasses.

5. The system of claim 1, further including a wireless radio disposed within the pair of eyeglasses, the wireless radio to transmit the respiration signal from the audio transducer to an electronic device separate from the pair of eyeglasses, wherein the processor is disposed within the electronic device.

6. The system of claim 1, wherein identifying the first respiration peak and the second respiration peak includes applying a data peak criteria to the respiration signal.

7. The system of claim 1, wherein:
   identifying the second respiration peak includes identifying a first valley between the first respiration peak and the second respiration peak; and
   identifying the first valley includes applying a data valley criteria to the respiration signal.

8. The system of claim 1, wherein the frequency-transformation of the respiration signal to generate the frequency-transformed signals further includes applying a 256-point rolling fast Fourier transform with a Hanning window smoother applied to the respiration signal.

9. A respiratory rate detection method comprising:
   generating a respiration signal from an audio transducer disposed within a pair of eyeglasses;
   frequency-transforming the respiration signal to generate frequency-transformed signals;
   summing magnitudes of the frequency-transformed signals within a breathing frequency range to generate a summed frequency respiration signal, the breathing frequency range including a minimum frequency of at least 2000 Hz and a maximum frequency of at most 2300 Hz;
   identifying a first respiration peak and a second respiration peak within the summed frequency respiration signal; and
   determining a respiration rate calculated as double a peak time delay between the first respiration peak and the second respiration peak.

10. The method of claim 9, wherein identifying the first respiration peak and the second respiration peak includes applying a data peak criteria to the respiration signal.

11. The method of claim 9, wherein frequency-transforming the respiration signal to generate the frequency-transformed signals further includes applying a 256-point rolling fast Fourier transform with a Hanning window smoother applied to the respiration signal.

12. At least one non-transitory machine-readable storage medium in an eyeglass apparatus, comprising a plurality of instructions that, responsive to being executed with processor circuitry of a computer-controlled device, cause the computer-controlled device to:
   receive a respiration signal from an audio transducer disposed within the eyeglass apparatus;
   frequency-transform the respiration signal to generate frequency-transformed signals;
   sum magnitudes of the frequency-transformed signals within a breathing frequency range to generate a summed frequency respiration signal, the breathing frequency range including a minimum frequency of at least 2000 Hz and a maximum frequency of at most 2300 Hz;
   identify a first respiration peak and a second respiration peak within the summed frequency respiration signal; and
   determine a respiration rate calculated as double a peak time delay between the first respiration peak and the second respiration peak.

13. The machine-readable medium in the eyeglass apparatus of claim 12, wherein the audio transducer is disposed within a bridge region within the eyeglass apparatus.

14. The machine-readable medium in the eyeglass apparatus of claim 12, wherein identifying the first respiration peak and the second respiration peak includes applying a data peak criteria to the respiration signal.

15. The machine-readable medium in the eyeglass apparatus of claim 12, wherein:

identifying the second respiration peak includes identifying a first valley between the first respiration peak and the second respiration peak; and identifying the first valley includes applying a data valley criteria to the respiration signal.

16. The machine-readable medium in the eyeglass apparatus of claim 12, wherein the instructions causing the computer-controlled device to frequency-transform the respiration signal to generate the frequency-transformed signals further includes instructions causing the computer-controlled device to apply a 256-point rolling fast Fourier transform with a Hanning window smoother applied to the respiration signal.

* * * * *